United States Patent

McCandless et al.

[11] Patent Number: 5,935,523
[45] Date of Patent: Aug. 10, 1999

[54] APPARATUS FOR ACCESSING A SEALED CONTAINER

[75] Inventors: William McCandless, Ringwood, N.J.; Spencer Lovette, Katonah, N.Y.; Hugo Lopez; Art Desanto, both of Brookfiedl, Conn.

[73] Assignee: Medical Laboratory Automation, Inc., Pleasantville, N.Y.

[21] Appl. No.: 08/864,829

[22] Filed: May 29, 1997

[51] Int. Cl.⁶ .................................................. G01N 35/10
[52] U.S. Cl. .............................. 422/100; 422/63; 422/65; 422/104; 436/43; 436/47; 436/49; 436/54; 73/864.24; 73/864.25; 141/330
[58] Field of Search ............................. 422/63, 65, 100, 422/104; 436/43, 47, 49, 54, 174, 180; 73/864.22, 864.24, 864.25; 141/276, 330, 329

[56] References Cited

U.S. PATENT DOCUMENTS

| | | |
|---|---|---|
| 2,855,929 | 10/1958 | Hein . |
| 3,991,627 | 11/1976 | Laird et al. ................................. 73/423 |
| 4,475,411 | 10/1984 | Wellerfors ............................ 73/864.24 |
| 4,478,095 | 10/1984 | Bradley et al. ....................... 73/864.21 |
| 4,577,514 | 3/1986 | Bradley et al. ....................... 73/863.01 |
| 4,662,231 | 5/1987 | Schaarschmidt et al. ........... 73/864.23 |
| 4,665,758 | 5/1987 | Schaarschmidt ..................... 73/863.32 |
| 4,721,137 | 1/1988 | Müller ...................................... 141/65 |
| 4,951,512 | 8/1990 | Mazza et al. ......................... 73/861.23 |
| 4,962,041 | 10/1990 | Roginski .................................. 436/150 |
| 5,212,992 | 5/1993 | Calhoun et al. ...................... 73/864.01 |
| 5,728,954 | 3/1998 | Uffenheimer ......................... 73/864.22 |

FOREIGN PATENT DOCUMENTS

| | | |
|---|---|---|
| 0 061 317 | 9/1982 | European Pat. Off. . |
| 0 452 892 | 10/1991 | European Pat. Off. . |
| 56-66761 | 6/1981 | Japan . |
| 62-273456 | 11/1987 | Japan . |

Primary Examiner—Long V. Le
Attorney, Agent, or Firm—Wolf, Greenfield & Sacks, P.C.

[57] ABSTRACT

A method and apparatus are provided for accessing a sealed container, and in particular a sealed container which is at a pressure other than atmospheric and which generally contains blood or other bodily fluid. A piercer and a probe are provided which are mounted to an XYZ positioning mechanism and are controlled such that the piercer passes through a stopper of the container, forming a cut therein through which the probe may subsequently enter the container. A foot mechanism is provided which is held against the stopper or seal for the container during piercer or probe removal for stripping purposes and through which the probe and piercer pass, the size and shape of the foot being such that, for both piercing and probing operations, it is over only a single container. The piercer and probe are operated such that the one not being used is in each instance in a raised position relative to the one being used. A novel lubrication station is provided in which the piercer is dipped prior to use to facilitate the piercing operation, to coat the cut and to minimize stopper debris. A wash station is also provided.

27 Claims, 12 Drawing Sheets

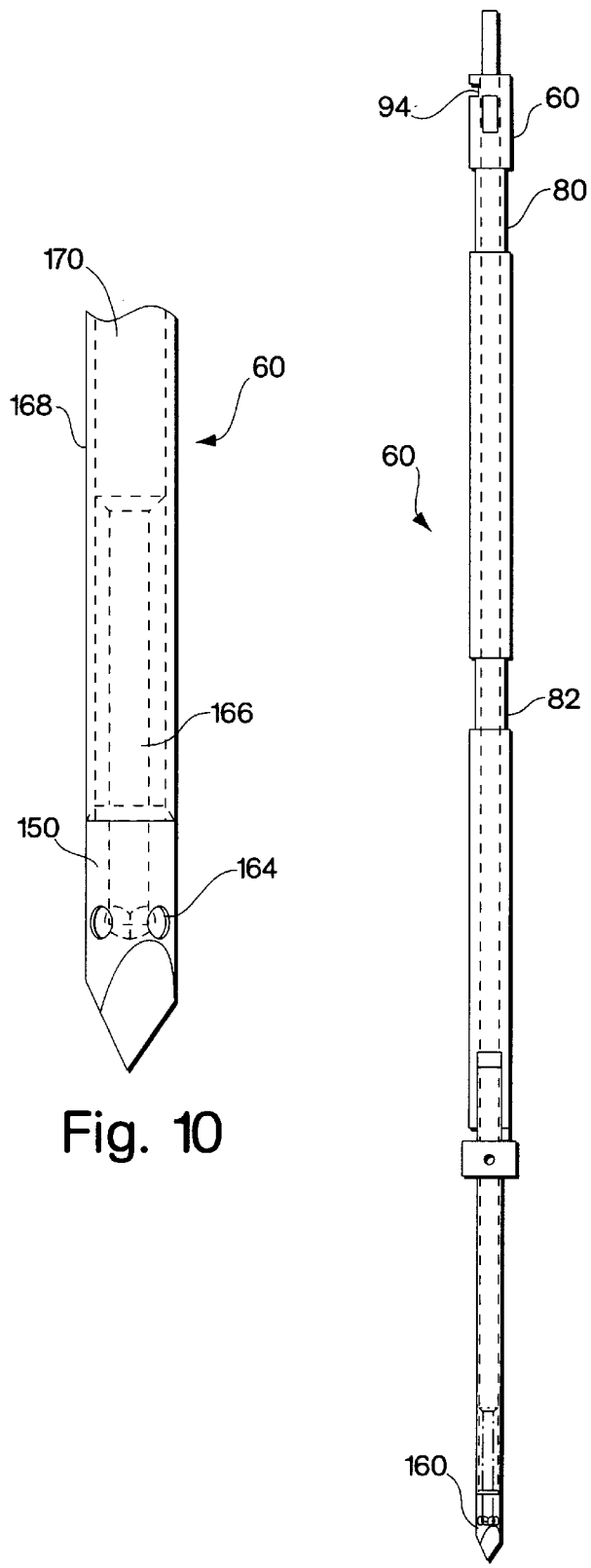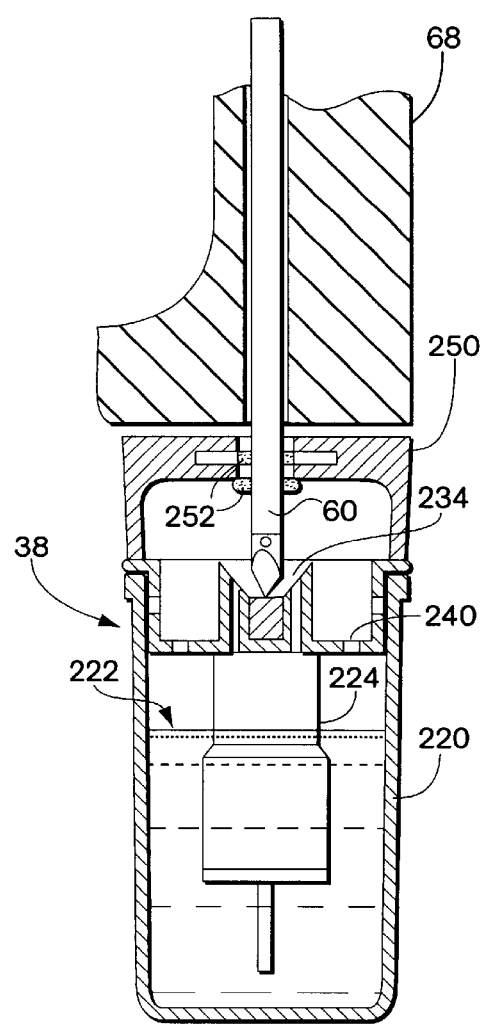
Fig. 10
Fig. 9
Fig. 13

APPARATUS FOR ACCESSING A SEALED CONTAINER

FIELD OF THE INVENTION

This invention relates to methods and apparatus for accessing a sealed container to remove the contents thereof, and in particular a fluid content, sense properties of such content or dispense material into the container, and more particularly to a method and apparatus for accessing blood or other bodily fluid from a sealed container, which container may have a reduced or increased pressure therein.

BACKGROUND OF THE INVENTION

Blood and other bodily fluids are sent in large quantities to medical laboratories where these fluids are processed and tested for diagnostic and other purposes. In order to minimize cost for such testing, the equipment and procedures utilized to process such samples are becoming increasingly automated so as to permit the procedures to be performed as quickly as possible with minimum labor. Further, since blood and other bodily fluid are now classified as hazardous substances, there are also safety reasons for minimizing handling of such specimens by people and for assuring that people do not come in contact with such samples.

The most popular way currently utilized for collected blood samples is to utilize a container, such as a glass tube, which is evacuated to be at relatively low pressure and is sealed at its open end with a rubber stopper or other puncturable seal. To draw a blood sample into the tube, one end of a double-ended needle is inserted into the patients vein and the other end of the needle is inserted through the stopper of the collection container, the partial vacuum inside the container drawing blood from the vein into the container.

When such blood filled containers arrive at the medical laboratory for testing, several procedures have heretofore been followed in processing the containers. Typically, the container is first "spun down" until all of the blood cells have settled to the bottom of the tube, leaving a layer of plasma or serum on top. The container may then have the stopper/seal removed and be placed in a sample rack for further processing, or the container may be unsealed and the plasma decanted into a cuvette or other open container for further processing. However, these procedures have several drawbacks. First, removing the seals is difficult to do automatically and is time consuming and expensive to do manually. Further, since the container is usually still under reduced pressure, there will be a sudden surge of air into the container when the seal is removed which can cause splashing of blood, something which is undesirable in all circumstances and is particularly undesirable when the process is being performed by a person because of the danger of contact with infected blood samples. Finally, the samples being in an open container exposes the samples to potential contamination in the laboratory, and the integrity of the samples can be better maintained if they remain in their sealed container.

For this reason, various schemes have been proposed for permitting aspiration of blood samples or other bodily fluid samples from the sealed container in which such samples are collected and shipped. However, these schemes also have limitations. For example, some such schemes have a sharp tipped probe pierce the seal to remove the sample. However, such probes tend to core the seal, which can result in the aspirating probe needle becoming plugged, thereby inhibiting aspiration of fluid from the container, and can also inhibit resealing of the container when the probe is removed, which resealing may be desirable in situations such as where the container may continue to be used for sample storage. Various schemes for preventing coring involve placing the needle opening on the side of the needle or otherwise deforming the needle opening. However, such schemes result in fluid from the needle coming out at an awkward angle when the fluid is to be dispensed, significantly complicating the design of the laboratory system.

For this reason, other schemes have utilized a canula shaped so as to minimize coring to puncture the seal, and have then passed an aspirating probe through the canula into the container to withdraw a desired quantity of fluid. These schemes also present a number of potential problems. First, the canula, being relatively large can abrade the rubber stopper, even if coring does not occur, causing rubber fragments which may be drawn into the probe with the plasma, potentially plugging the probe and destroying the precision and integrity of the samples. Second, the canula presents a temporary opening in the container seal through which contaminants may enter the container. Finally, the use of the canula limits flexibility as to how a number of containers on a rack, cassette of the like may be sampled. In particular, it may be desirable to take a first sample from all of the containers of a given group for a particular test, and to then go back and take a second sample from each such container for a subsequent test. However, these systems envision the canula remaining in the stopper for the entire test, and not being removed and reinserted. Therefor, unless a number of canulas are provided, something which is generally not feasible, all samples required from a given container must be taken before the canula is removed from the container and inserted in a subsequent container.

Finally, one scheme involves using a piercer to form an opening or cut in the seal and then passing a needle or probe into the container through the cut to aspirate or otherwise access the fluid. While this scheme overcomes some of the limitations of the procedures discussed earlier, it also has limitations. In particular, it can leave a ragged opening or cut in the seal, resulting in seal fragments as debris which can potentially clog the probe or adversely affect the integrity of samples. Further, where samples are being taken from multiple containers, as would be the case in a medical laboratory, the containers are preferably mounted close together in a rack and are not secured in the rack. The spacing between the piercer and probe in the prior art system limits how closely the containers can be mounted and no effective way is provided for stripping the piercer/probe from the seal for a loosely/rack mounted container.

Another potential problem with all of the above schemes is that, at some point during the handling of the container, blood cells or other debris from the sample may accumulate under the stopper. Since it is desired that only the plasma or serum be utilized for most tests, blood cells in a specimen may contaminate the specimen, rendering the test less valid. Such blood debris may also be misinterpreted by electronic level sensing modules frequently used in such systems, resulting in the improper collection or aspirating of the fluid. None of the current schemes adequately deal with this potential problem.

Another problem not fully dealt with in the prior art is the need to quickly, but effectively wash and dry both the piercer and probe between samplings so as to prevent any contamination of successive samples by these elements. Other improvements in design are also required to facilitate high speed operation, with at least four accessing operations a minute, while permitting accurate, contamination free operation and minimizing maintenance problems.

A need therefor exists for an improved method and apparatus for collecting blood or other bodily fluids from sealed containers or otherwise accessing such containers either to collect a desired fluid or other substance therefrom, to sample or sense properties of the substance contained in the container, or to dispense material into such container. Similar needs can exist when accessing other fluids from a sealed container such as closed sample vials on chromatography samplers or quality control sampling of any materials packaged in containers with rubber stoppers.

SUMMARY OF THE INVENTION

Therefor, in accordance with the above, this invention provides a method and apparatus for accessing fluid in a container, which container is sealed by a piercable seal. The apparatus includes a piercer, a probe having a hollow tube into which fluid from the container may be drawn, a first mechanism for moving both the piercer and the probe in the Z direction, which direction is perpendicular to the seal, and a second mechanism which moves the first mechanism, including the piercer and the probe, in X and Y directions, which directions are substantially perpendicular to the Z direction. For preferred embodiments, at least one of the piercer and probe do not normally move with the first mechanism, but are selectively attachable to be moved therewith. Controls are provided for operating the first and second mechanisms to have the piercer pierce the seal of a container while, for preferred embodiments, the probe is maintained a selected distance above the seal, to withdraw the piercer from the seal, leaving a cut in the seal, and to then have the probe pass through the cut in the seal to enter the fluid in the container while, for preferred embodiments, the piercer is maintained at a selected distance above the seal.

For preferred embodiments, the apparatus also includes a foot through which the piercer and probe pass, the foot being at the bottom of a foot mechanism mounted to normally move with the first mechanism in the Z direction. The controls preferably lock the foot mechanism against Z direction movement when the foot is lowered into contact with the seal of a container and release the foot mechanism to again move with the first mechanism when the first mechanism has risen to a predetermined position. Where there are a plurality of containers to be accessed, which containers are mounted adjacent each other with a selected space therebetween, the lower seal-contacting surface of the foot has a size and shape such that the lower surface of the foot contacts only the seal for the container being accessed, and does not contact the seal for any adjacent container when the foot is lowered either for the piercing of the seal by the piercer or for entry of the probe through the seal. The foot mechanism and at least one of the piercer and probe (the piercer for the preferred embodiment) are normally moved downward in the Z direction by gravity, such downward movement being restrained by detents limiting how far below the first mechanism they may fall. A first locking component operated by the controls locks the foot mechanism against Z direction movement under selected conditions and a second locking component is operated by the controls under selected condition to lock the at least one of the piercer and probe (the piercer for the preferred embodiment) to the first mechanism to move therewith in the Z direction. For the preferred embodiment, the piercer normally rests within, and is detented against independent downward movement by the foot. For this embodiment, when the second locking components locks the piercer to the first mechanism, the first mechanism moves the piercer downward and upward through the foot.

For the preferred embodiment, a lubrication station is also provided, the controls operating the first and second mechanisms to position the piercer over and to dip the piercer into the lubrication station before moving the piercer to pierce the seal. The lubrication station preferably includes a means which controls the depth to which the piercer is lubricated and a means for removing excess lubricant from the piercer before the piercer is moved to pierce the seal. The lubricant on the piercer permits the piercer to pass through the stopper with minimum abrasion, thereby substantially eliminating stopper debris which may potentially result from such abrasion and the problems associated with such debris.

The piercer preferably has a plurality of vent holes circumferentially positioned above its tip and a channel leading from the vent holes out of the piercer. A suction source is connected to the channel, with the controls operating the suction source to apply suction to the vent holes from a time before the piercer pierces the seal to a time after the piercer is removed from the seal. The piercer, including the vent holes, has smooth rounded edges to minimize abrasion of the seal as the piercer passes through, further reducing the generation of stopper debris by the piercer. The suction applied to the piercer is operative, when the piercer is positioned with the vent holes under the stopper, to remove any blood cells or other solid debris which may have accumulated under the stopper, thereby preventing false liquid level sensings resulting from such debris and preventing contamination of plasma samples by such debris. The suction on the vent holes as the piercer passes through the stopper also sucks out any stopper debris caused by the piercer cutting through the stopper so as to further minimize this potential problem.

To further assure against the aspirating of cell debris with a plasma sample, a liquid level detection mechanism of which the probe is a part causes the controls to abort an accessing/aspiration of fluid from a container if such detector generates an output before the probe has advanced sufficiently into the container to contact fluid. The probe preferably also has vent holes at a selected distance above its tip through which pressure inside and outside the container may be equalized when the probe enters the container. The controls may operate in conjunction with the liquid level detection mechanism to control the first or Z direction mechanism so that the probe enters fluid in the container to a depth between the vent holes and the probe tip and is lowered as fluid is removed by the probe to maintain the desired depth for the probe in the fluid.

Finally, a wash station is provided for preferred embodiments for both the piercer and probe. The controls operate the first and second mechanisms to move the piercer and probe over and to immerse the piercer and probe in the wash station when accessing operations for a container have been completed. An air pressure source may be connected to the channel leading to the vents for the piercer and probe during the wash operation to blow air out through the vent holes thereby keeping wash fluid out of the holes and channels. The wash station may have a separate well for the piercer and the probe, with the controls causing a washing fluid to flow through each well during a first part of a wash cycle to wash the element therein and causing air to be flowed through the well for a second part of the wash cycle to dry the corresponding element.

The method for accessing a fluid in the sealed container includes the steps of:

(a) positioning a foot mechanism and a piercer over substantially the center of the seal for a container to be accessed;

(b) moving both the foot mechanism and piercer down until a foot at the bottom of the foot mechanism contacts the top of the seal;

(c) locking the foot mechanism in contact with the seal;

(d) moving the piercer down through the foot and the seal to form a cut in the seal;

(e) moving the piercer upward to, in conjunction with the foot holding the seal against upward motion, strip the piercer from the seal;

(f) unlocking the foot mechanism and moving both the foot mechanism and the piercer upward;

(g) positioning the foot mechanism and the probe over the cut in the seal made by the piercer;

(h) moving the foot mechanism and the probe down until the foot contacts the top of the seal and locking the foot mechanism in that position;

(i) moving the probe down through the cut in the seal made by the piercer and immersing the tip of the probe in the fluid;

(j) accessing the fluid through the probe;

(k) moving the probe upward to, in conjunction with the foot holding the seal against upward motion, strip the probe from the seal; and (l) unlocking the foot mechanism and moving both the foot mechanism and the probe upward.

For preferred embodiments, from a time before the piercer enters the seal until a time after the piercer leaves the seal, suction is applied through a channel in the piercer and the vent holes circumferentially formed about the tip of the piercer to remove debris. For preferred embodiments, before step (a) is performed, the piercer is positioned over a lubrication station, the piercer is moved downward to dip the tip of the piercer up to a selected depth into a lubricant, and the piercer is raised out of the lubrication station. When the piercer is raised out of the lubrication station, the step of wiping excess lubricant from the tip of the probe may also be performed.

During step (i) when the probe enters the container, pressure inside and outside of the container may be equalized by permitting air to enter the container though vent holes in the probe. The probe is perferably lowered into the fluid to a depth between the vent holes and the probe tip, with the probe being lowered as fluid is withdrawn to maintain the depth of the probe in the fluid within such range.

The process may also include the steps, performed after operations for a given container have been completed, of positioning the piercer and probe over a wash station; lowering the piercer and probe to immerse both in the wash station; performing a wash operation on the piercer and probe; and raising the piercer and probe out of the wash station. Where at least one of the piercer and probe has vent holes leading to a channel therein, during times that the piercer and probe are in the wash station, air is blown out through the vent holes, thereby keeping wash fluid out of the holes and channels. Where the wash station has separate wells for the piercer and the probe, the washing step may include the steps of flowing a washing fluid through each well during a first part of a wash cycle to wash the piercer/probe therein, and flowing air through each well during a second part of each wash cycle to dry the piercer/probe.

The invention also includes a mechanism for iteratively applying a liquid coating to an element tip up to a selected length or depth thereof, which mechanism includes a fluid reservoir and a pump having a top portion and a bottom portion, with a sealed chamber normally formed therebetween. The top portion is movable vertically relative to the bottom portion to change the size of the chamber. The pump is positioned in the reservoir and has a cup at the top of its top portion, the cup having a depth substantially equal to the length of the element tip to be coated. The top portion is moved down to decrease the size of the chamber when the element tip is pressed into the cup, with a means being provided to return the chamber to its original size when the element tip is no longer pressed into the cup. A first normally-closed valve is provided which is opened when the chamber size is decreased to permit a quantity of liquid in the chamber, which quantity is at least sufficient to cause the cup to be filled, to flow from the chamber into the cup; and a second normally-closed valve is provided which is opened when the chamber is being returned to its original size to permit liquid to flow from the reservoir into the chamber to substantially refill the chamber with liquid. For the preferred embodiment, the quantity of liquid which flows into the cup from the chamber is sufficient to cause some liquid overflow from the cup, thereby assuring that the cup is completely full. A path may be provided for liquid overflow to return to the reservoir or a path may be provided for such liquid overflow to flow to a waste drain. For the preferred embodiment, the mechanism is a lubrication module, with the liquid therein being a lubricant. A wiper is preferably positioned to be passed through by the element tip after leaving the cup to remove excess liquid from the tip, with the wiper being a brush for the preferred embodiment.

The foregoing and other objects, features and advantages of the invention will be apparent from the following more particular description of a preferred embodiment of the invention as illustrated in the accompanying drawings.

IN THE DRAWINGS

FIG. 9 is a side view of a piercer assembly suitable for use in practicing the teachings of this invention.

FIG. 10 is an enlarged side view of the tip for the piercer mechanism shown in FIG. 9.

FIG. 13 is a partially cutaway diagrammatic side view of a lubrication station suitable for use in practicing the teachings of this invention.

DETAILED DESCRIPTION

Figure 1:
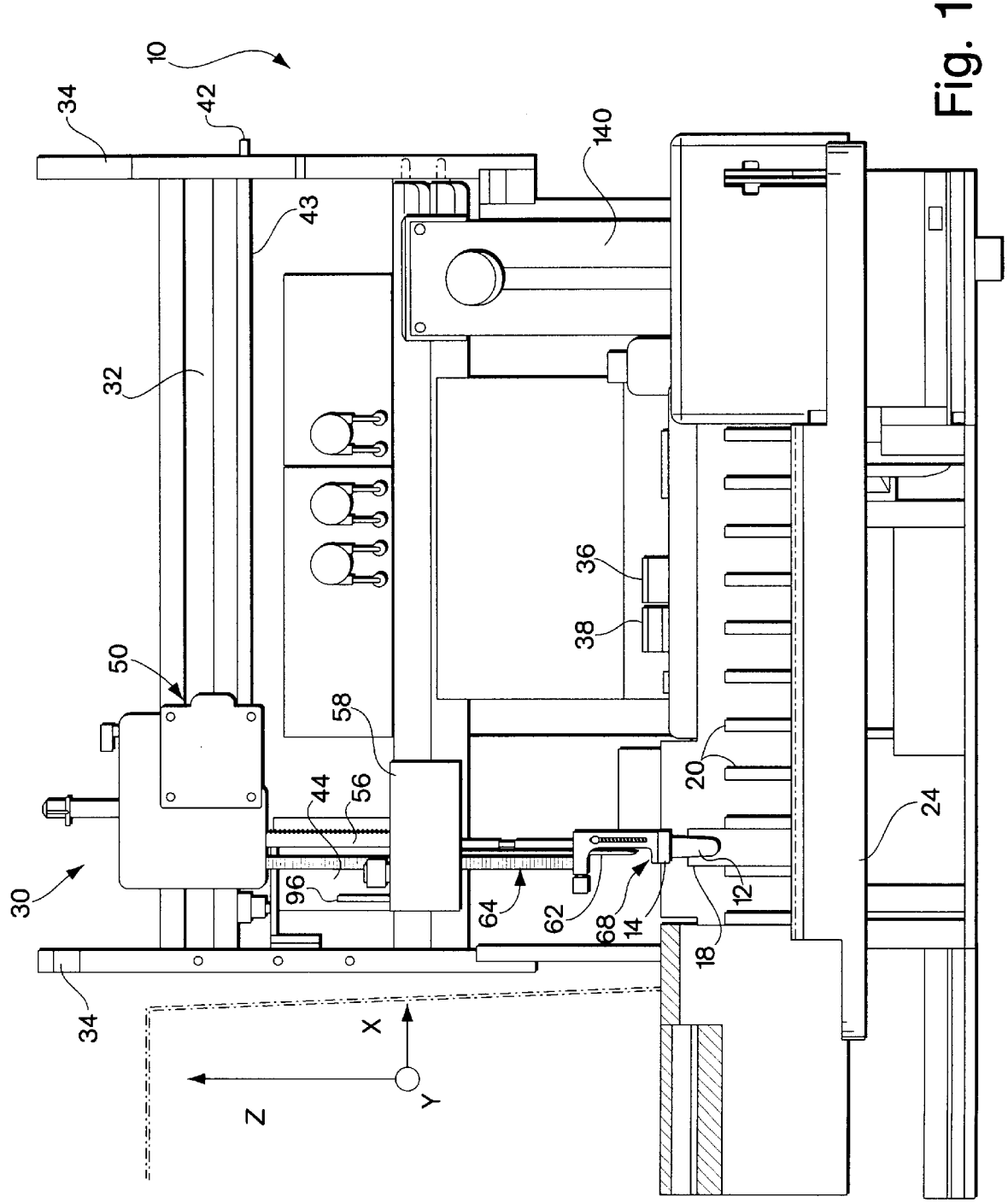
FIG. 1 is a semidiagramatic front view of a closed tube blood handling system which utilizes the teachings of this invention.
Figure 2:
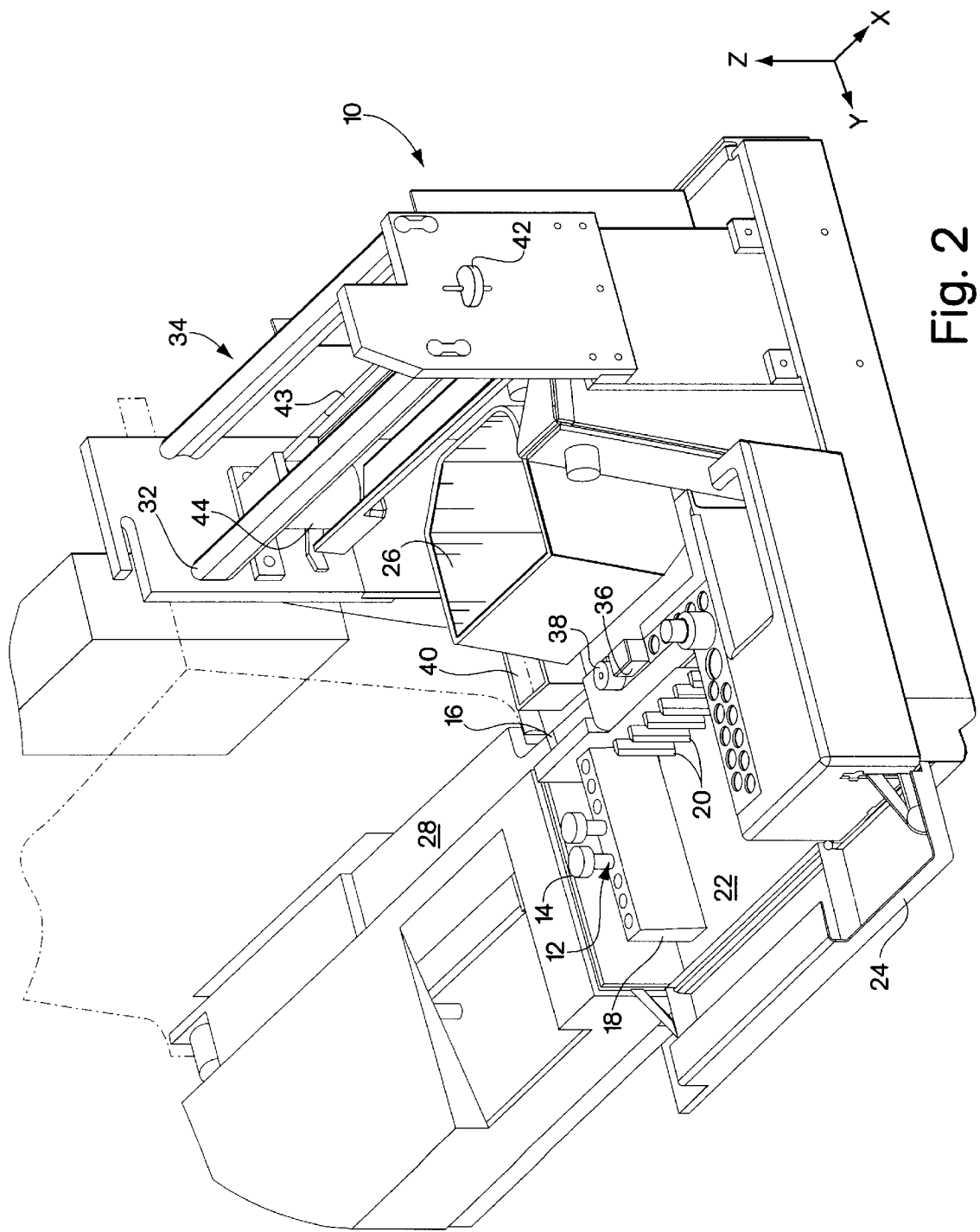
FIG. 2 is a front/top/right side perspective view of the system shown in FIG. 1 with the piercer, probe and piercer-probe positioning mechanisms omitted.

Referring first to FIGS. 1 and 2, a laboratory blood analyzer system 10 is shown which system is designed to sample blood or other bodily fluid contained in a tube or other container 12, which container is sealed by a piercable cap or seal 14, and to decant the samples into a reaction cuvette 16. Tubes 12 are mounted in removable racks 18 which racks are mounted between corresponding supports 20 at a tube or container mounting station 22. A cover 24, which is shown open in FIG. 2, is opened to insert and remove racks 18, each of which may contain a plurality of tubes 12 mounted adjacent each other, and is otherwise closed. Cuvettes 16 are transferred, using techniques which do not form part of this invention, from a hopper 26 to a transport channel 28 along which they may be moved to a testing and analysis station of a type known in the art.

System 10 has a positioning mechanism 30 which is moved in the X direction along rail 32, which rail is fixed at its ends in a housing structure 34. The system also includes a wash station 36, a lubrication station 38 and a tip wash 40 which is located at the home position for positioning mechanism 30. Lubrication station 38 is positioned adjacent and to the right of the location where decanting occurs for a cuvette 16 and wash station 36 is located adjacent and to the right the lubrication station.

Figure 3:
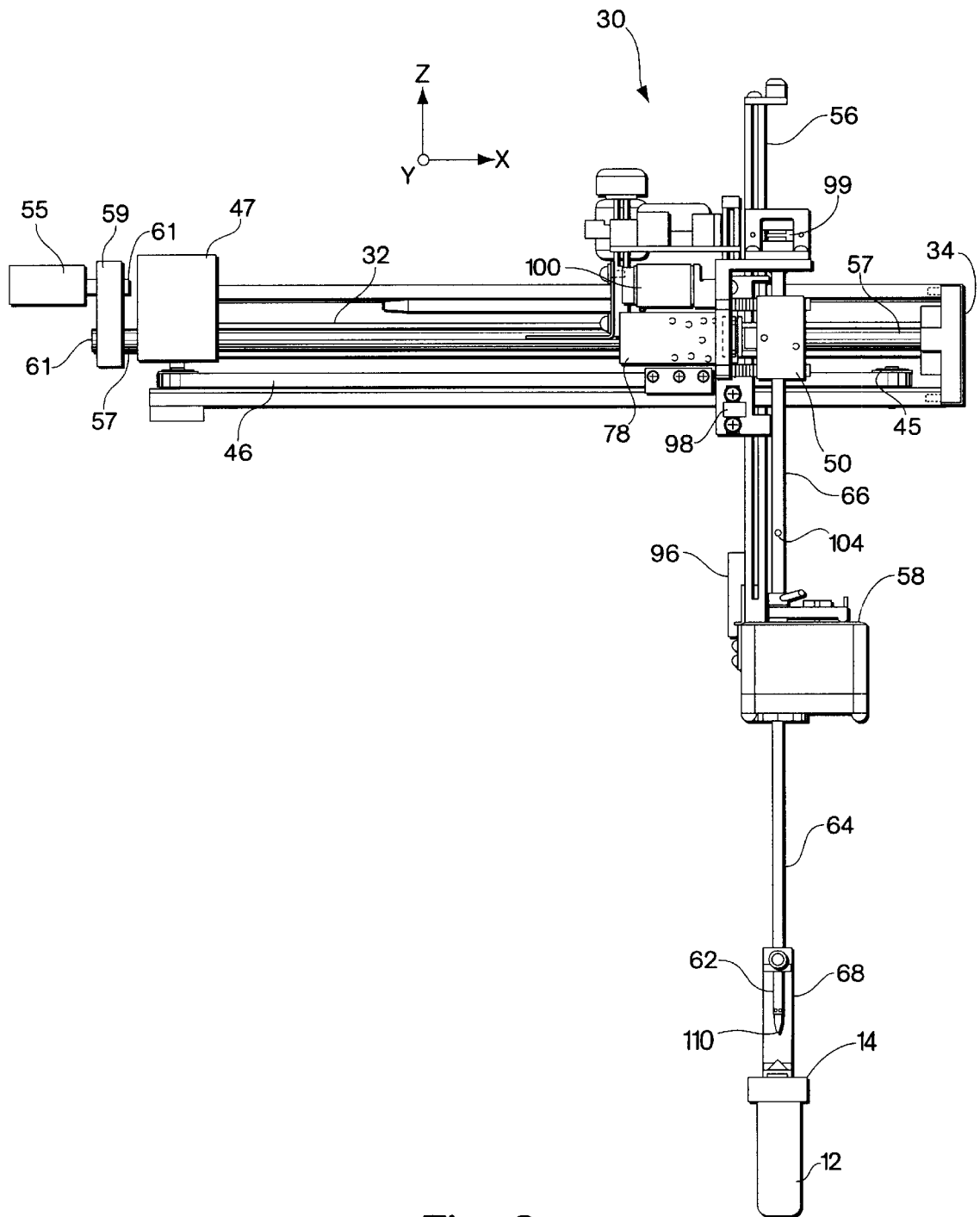
FIG. 3 is enlarged and more detailed view of the probe and piercer positioning mechanism for the system of FIG. 1.
Figure 4:
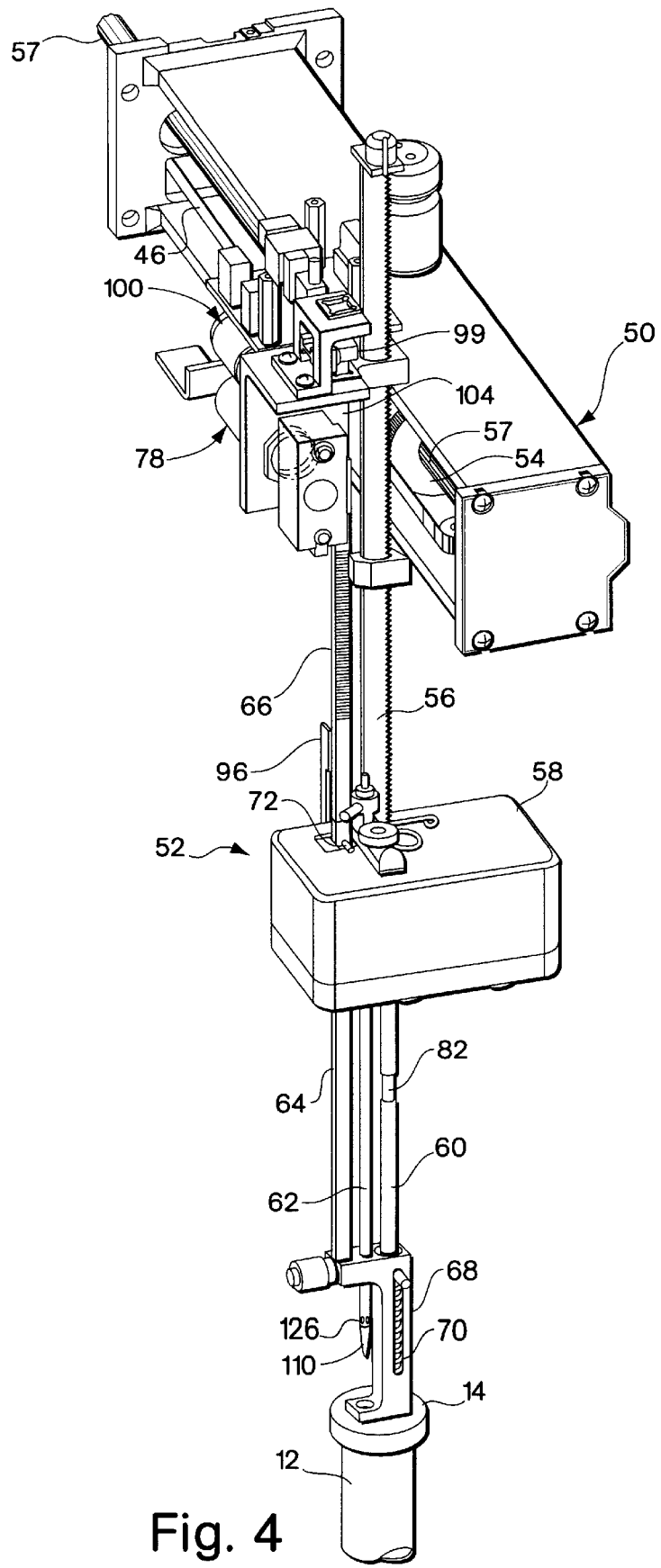
FIG. 4 is a further enlarged perspective view of a portion of a mechanism shown in FIG. 3.
Figure 5:
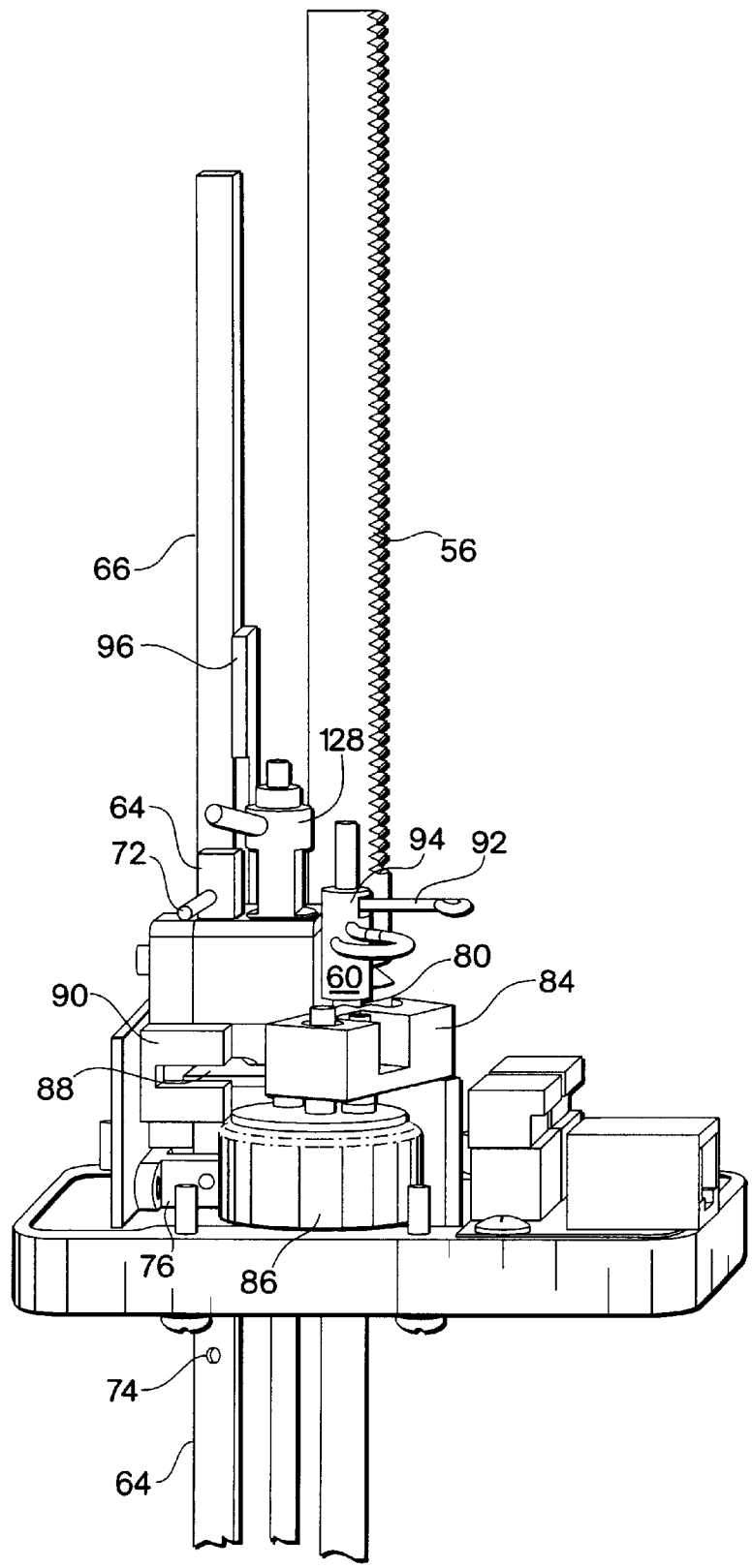
FIG. 5 is a view of the Z direction control mechanism for the positioning mechanism of FIGS. 3 and 4 with its cover removed.

FIGS. 3–5 show the positioning mechanism 30 in greater detail. This mechanism includes pulley 42 and belt 43 driven by motor 44 for moving mechanism 30 in the X direction, and pulley 45 and belt 46 driven by motor 47 for moving mechanism 30 in the Y direction on cantilever arm 50. Vertical or Z-direction movement of a piercer/probe mechanism 52 is effected by a gear 54, driven by a suitable motor 55, spline 57, belt 59 and pulleys 61, driving a rack 56 which terminates in assembly 58, the insides of which are shown in FIG. 5. A piercer 60, and a probe 62 extend downward from assembly 58. A shaft 64 extends through assembly 58 and terminates in a linear rack 66, shaft 64 and rack 66 forming part of a foot mechanism which also includes a guard or foot element 68. Piercer 60 is normally mounted in and held in foot 68 by spring 70, spring 70 normally providing sufficient friction to the lower end of piercer 60 to hold the piercer 60 in foot 68, but not sufficient friction to prevent movement of the piercer through the foot when the piercer is engaged by the Z drive mechanism in a manner to be described later. Shaft 64 has a stop or detent 72 which engages the top cover of assembly 58, inhibiting the fall of the foot mechanism under the action of gravity so that this mechanism moves down with assembly 58 under the action of gear 54 and rack 56. A hole 74 in shaft 64 is detected by a sensor, for example an optical sensor 76, in assembly 58 (FIG. 5). The detection of hole 74 by sensor 76 is utilized to control the operation of a linear solenoid 78 which, when operated, engages and locks rack 66 to prevent vertical upward movement of the foot mechanism.

As indicated earlier, piercer 60 is normally not attached to move vertically with assembly 58, and instead moves vertically with foot 68 and the mechanism to which it is attached under the action of either gravity or detent 72 coacting with the cover of assembly 58. However, piercer 60 has an upper groove 80 (FIG. 5) and a lower groove 82 (FIG. 4) formed therein which grooves coact with a pawl 84 driven by a rotary solenoid 86 to lock the piercer to the vertical movement of assembly 58 at selected positions of the piercer relative to assembly 58 and under selected conditions to be discussed later. To assure that the pawl 84 has properly engaged piercer 60 under the selected conditions, a flag 88 may be provided with the pawl and is in position to be sensed by rotary solenoid sensor 90 when the pawl is fully engaged in a groove 80/82. As a protection against piercer 60 remaining positioned in a cover or stopper 14, a clip 92 is provided which fits in a groove 94 in a top portion of piercer 60 which extends above the cover of assembly 58, and coacts with the top of assembly 58 to assure the withdrawal of piercer 60. When mechanism 58 is in its fully raised or maximum Z position, which may also be referred to as a home position, a flag 96 attached to assembly 58 blocks a Z home sensor 98 attached to mechanism 30 (FIG. 3). Once assembly 58 moves away from its home position, sensor 98 is unblocked so as to no longer produce an output. A pinch valve 100 is also provided which valve is open when the tip 112 of probe 62 is under stopper or cap 14 to equalize pressure inside and outside of container 12 in a manner to be described later.

Further, there is a sensor 99 (FIGS. 3 and 4) which looks for a hole 104 in rack 66 going by while the linear solenoid 78 should have the rack locked in place. If this sensor detects hole 104, indicating that foot 68 is moving with assembly 58, it sends a signal to the system control to initiate corrective action. The system 10 is controlled by a microprocessor 11 (FIG. 2) or other suitable control processor, which may be programmed, hard wired, or operate as a hybrid of hardware and software to cause the system 10 to operate in the manner described later.

Figure 6:
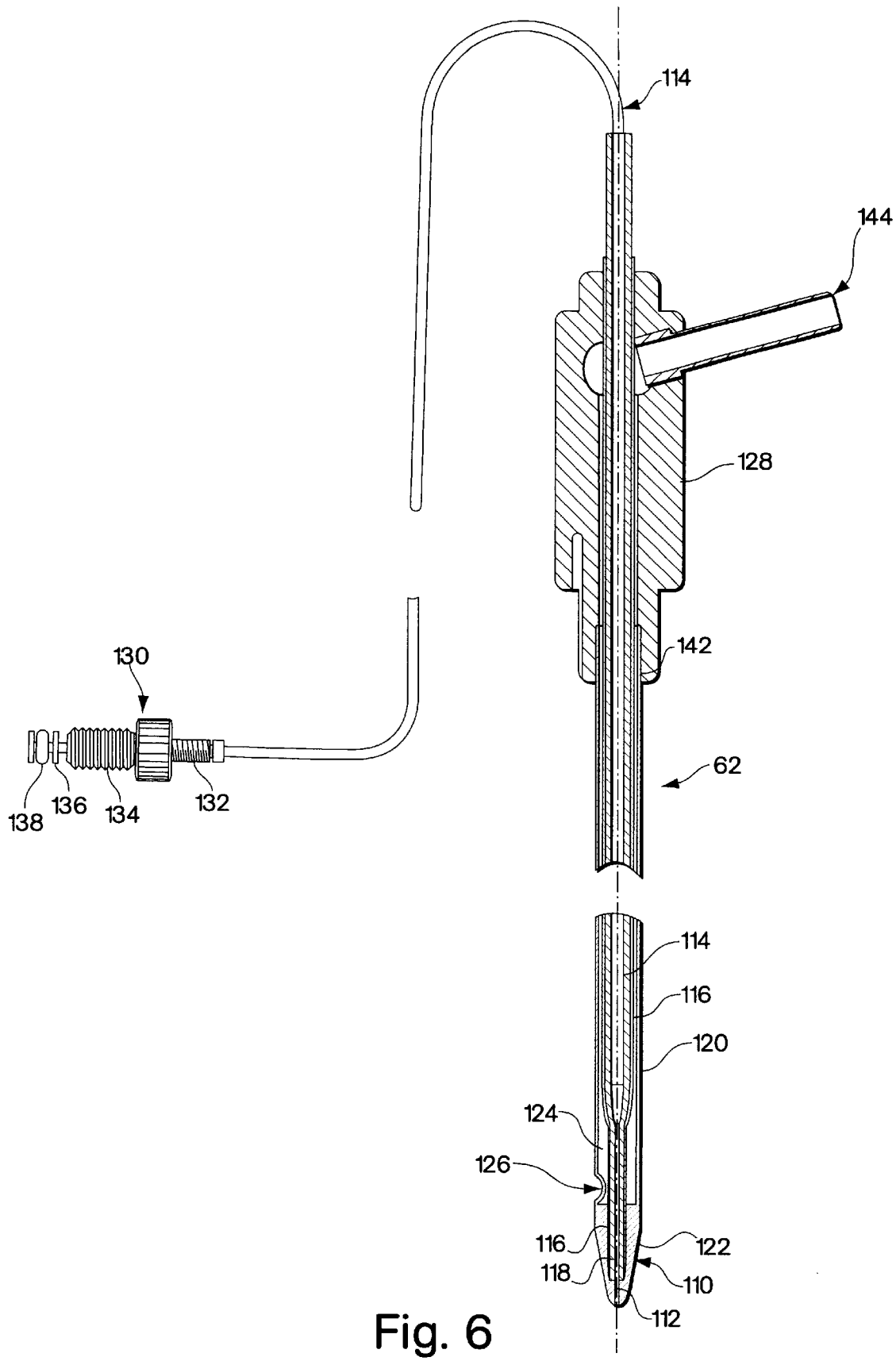
FIG. 6 is a partially cutaway view of a probe mechanism suitable for use in practicing the teaching of the invention.

FIG. 6 is a more detailed view of the probe mechanism 62. Probe 62 has a probe tip I 10 with an opening 112 formed in the bottom thereof which leads into an aspirating tube 114. Tube 114 is preferably formed of a material with a low surface adherence such as Teflon. Aspirating tube 114 is surrounded by an inner tube 116 which may be of a metal such as stainless steel. Inner tube 116 is bonded to tip 110 at 118, for example by epoxy bonding. An outer or vent tube 120, which may also be of a metal such as stainless steel, is epoxy bonded at its end to tip 112 (bond 122) and is spaced from inner tube 116 to form an air channel 124. One or more vent holes 126, four vent holes for a preferred embodiment, are formed in outer tube 120 at a point just above tip 110, the vent holes providing access to channel 124. The edges of all the vent holes are rounded and the outer surfaces are for example electropolished to make these surfaces as smooth as possible so as to minimize the creation of stopper debris as the probe enters and leaves the stopper.

Figure 7:
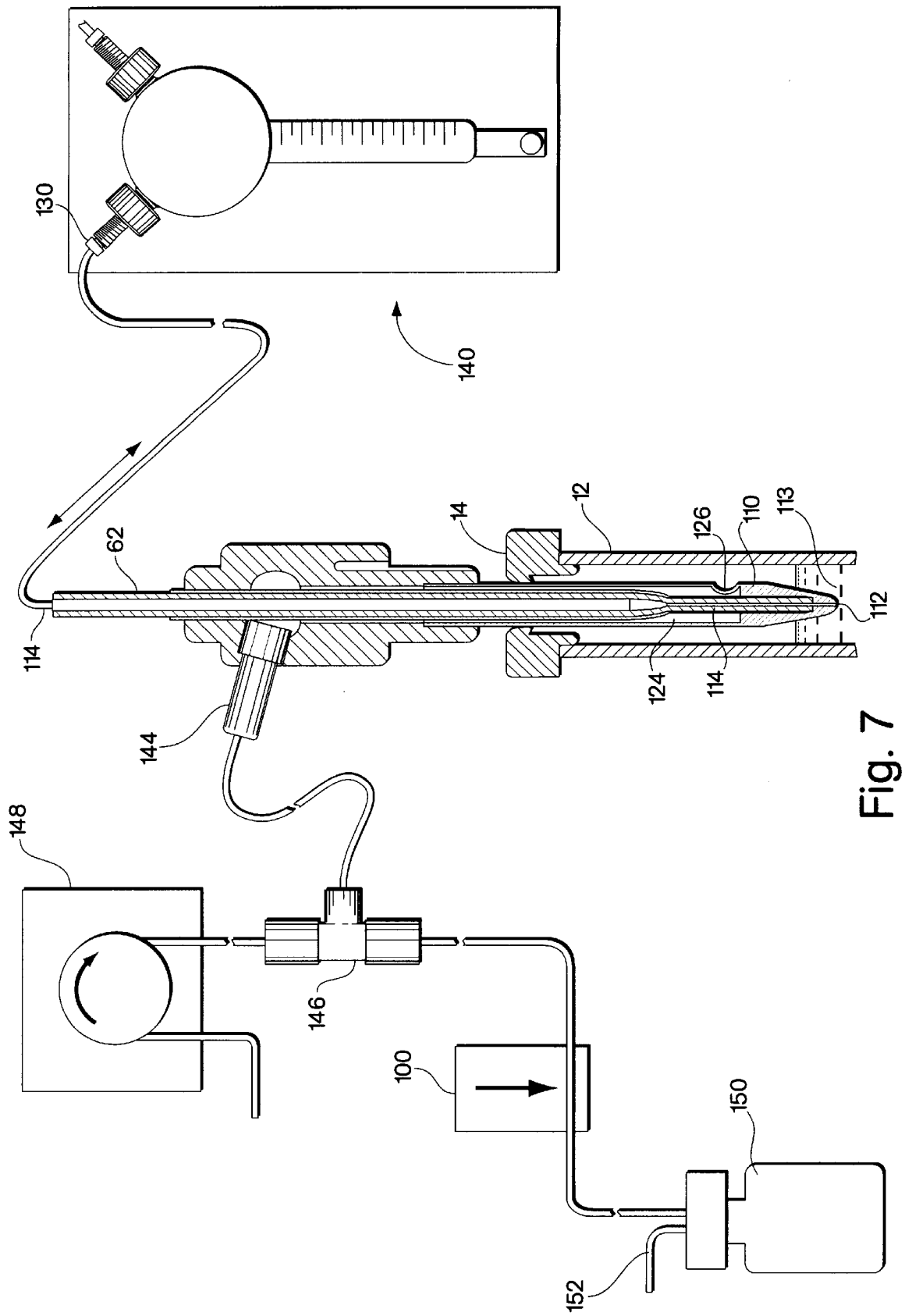
FIG. 7 is a diagrammatic view of the probe mechanism and related components with the probe in position to aspirate fluid from a container.

Tube 114 passes through an air manifold 128 to a connector 130 which includes a strain relief fitting 132, a stainless steel connection fitting 134, a washer 136 and an O-ring 138. Connector 130 leads to positive displacement pump 140 (FIG. 7) which may be utilized in standard fashion to either aspirate or dispense fluid from probe 62, and to pump fluid therein.

Channel 124 leads into air manifold 128, with outer tube 120 terminating at 142 in the manifold. The manifold leads through a vent output or fitting 144 to a T junction fitting 146. One connection to T fitting 146 is from a Peri pump 148. The other connection from the fitting leads to pinch valve 100 and through the pinch valve and a vent trap 150 to a line 152 leading to ambient air.

Figure 8:
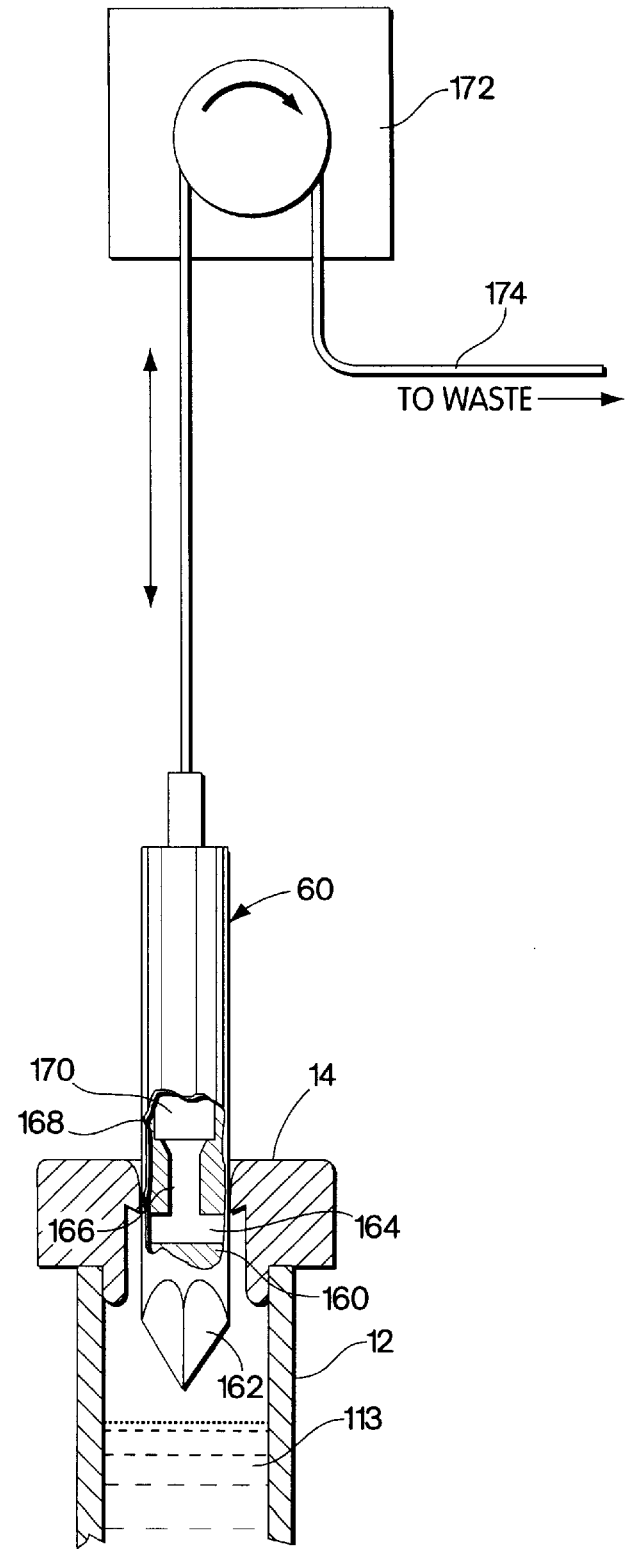
FIG. 8 is a partially cutaway, partially diagrammatic side view of a piercer mechanism in accordance with the teachings of this invention when positioned in a container to remove debris therefrom.

FIGS. 8, 9, and 10 illustrate piercer 60. Piercer 60 has a tip 160 having a sharpened three edge point 162. A plurality of vent holes 164, for example four holes, are formed in probe tip 160 which holes communicate with a channel 166 formed in the tip. Tip 160 is welded to a tube 168 having an opening 170 which communicates with channel 166 and leads from the piercer through a piercer pump 172 to a waste line 174. The manner in which the piercer is utilized, as illustrated in FIG. 8, to remove debris from container 12, and in particular debris such as blood cells located under cap or stopper 14, will be described later. The grooves 80 and 82 formed on the outside of piercer 60 have been previously mentioned. As for the probe, the vent holes of the piercer are rounded and its outer surface smoothed to minimize the generation of stopper debris.

Figure 11:
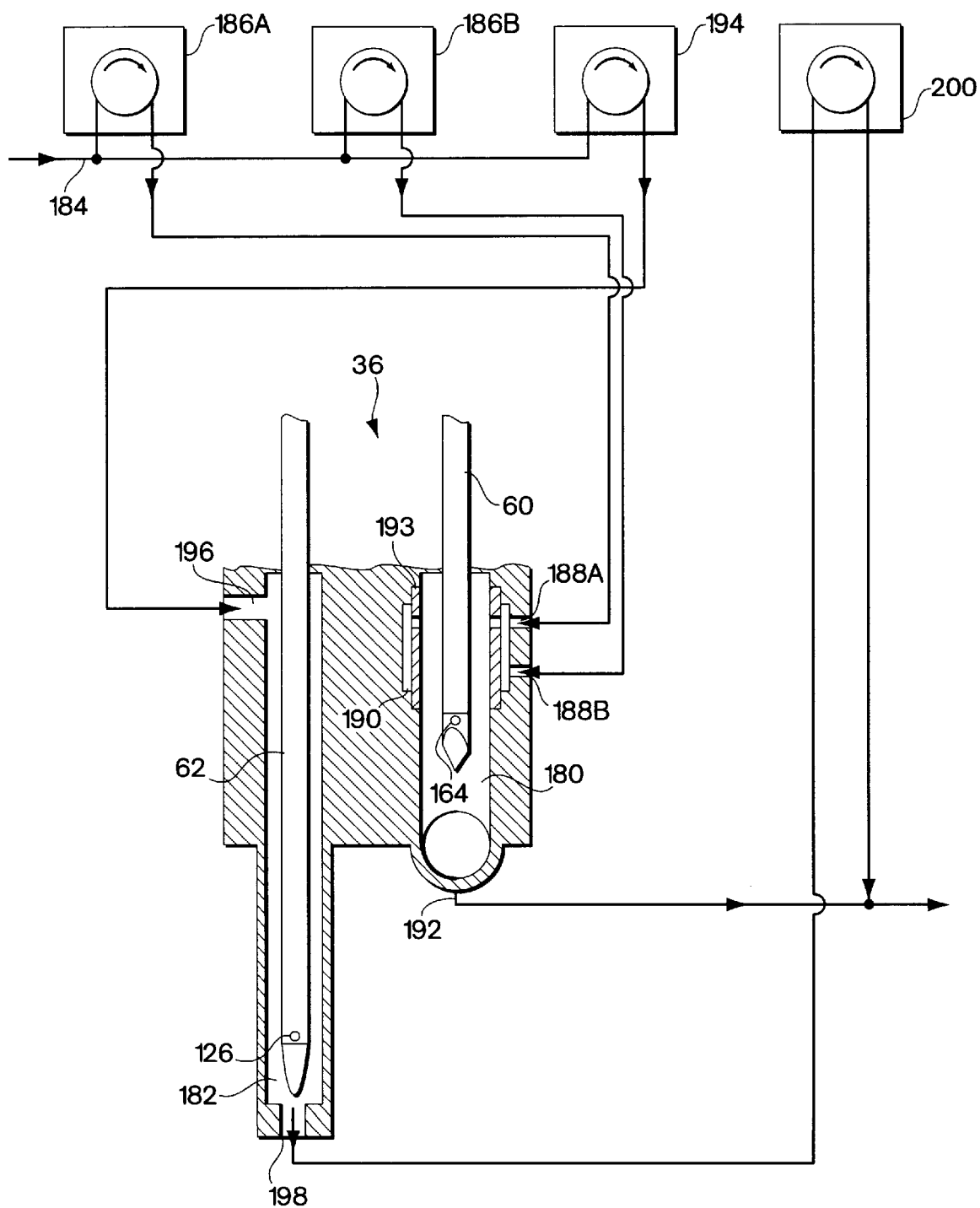
FIG. 11 is a diagrammatic view of a wash station with the piercer and probe mounted therein, which station is suitable for use in practicing the teachings of this invention.
Figure 12:
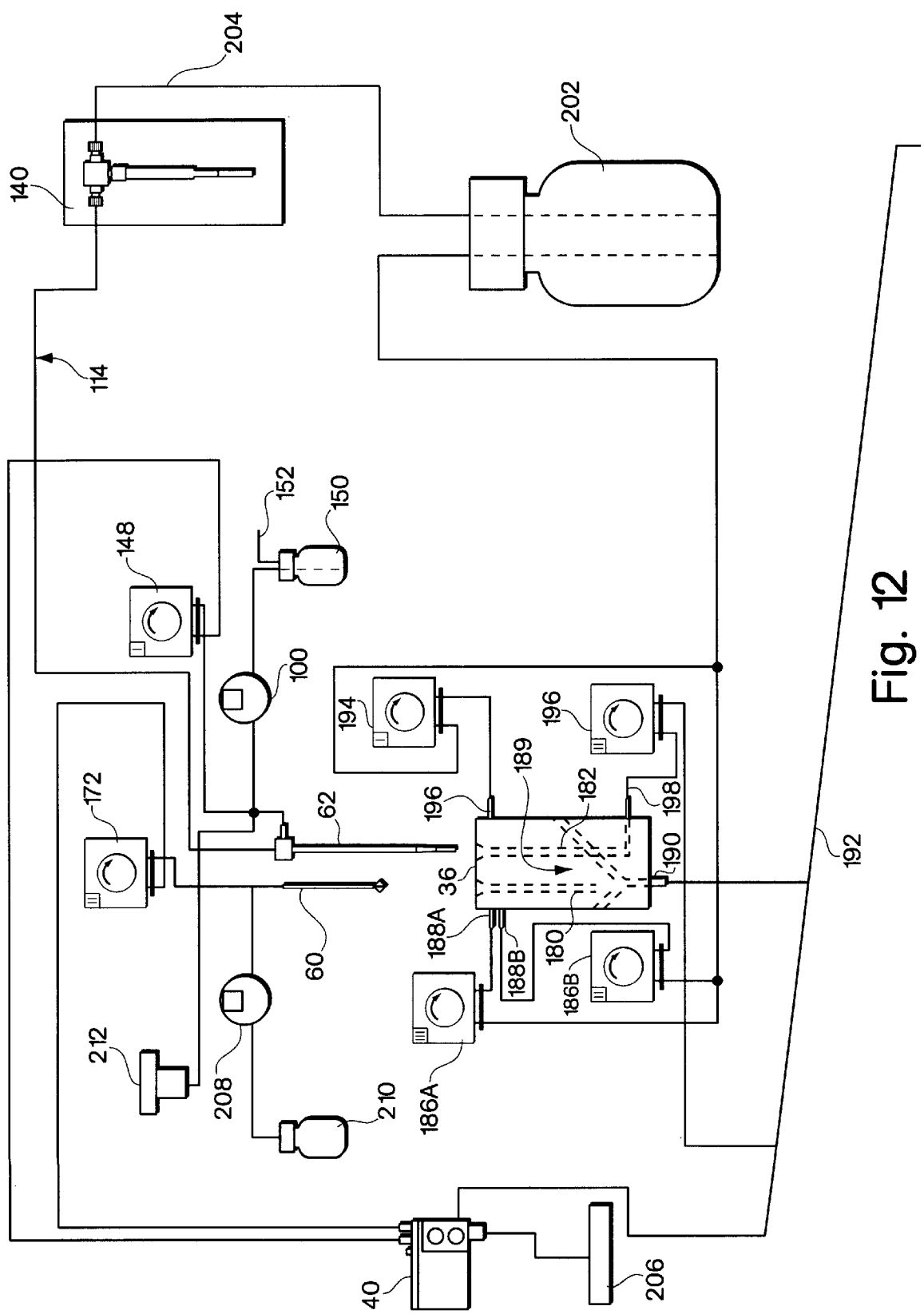
FIG. 12 is a diagrammatic view of the hydraulics for the system of FIGS. 1 and 2.

FIGS. 11 and 12 illustrate wash station 36, with FIG. 12 also illustrating the hydraulics for remaining portions of the system. Referring first to FIG. 11, it is seen that wash station 36 has a first well 180 for the piercer and a second well 182 for the probe. When the piercer 60 and probe 62 are in their respective wells 180, 182, the probe is at a lower level than the piercer. Water or other suitable wash fluid is pumped in through line 184 and pumps 186A, 186B to a pair of fluid inlets 188A, 188B respectively of well 180. Inlets 188 lead to a channel 190 which then allows the wash fluid to be jetted through twelve radially place holes in core 193, which are all aimed at the piercer. This results in an even distribution of fluid spray over the outer surface of the piercer body and tip as it is withdrawn from the well. The wash fluid exits well 180 through a dump sump 189 leading to a port 191 and a waste line 192.

Wash fluid in line 184 also passes through pump 194 to fluid inlet or port 196 leading to well 182, this fluid washing the outside of the lower portion of probe 62, including the tip of the probe. Wash fluid with any blood or other substance washed from the probe is removed through an outlet port 198 under the action of pump 200 to waste line 192.

A wash fluid reservoir or bottle 202 is provided from which wash fluid may be withdrawn, for example through straws, to a first feed line 204 leading into positive displacement pump 140 to fill probe 62 above the samples, and between samples, in a manner known in the art. Fluid from reservoir 202 is also applied to pumps 186 and 194.

FIG. 12 also shows the tip wash station 40, with its connection to waste line 192 and a connection to an overflow tray 206. The tip wash station 40 is used to wash the tip 110 of the probe 62 when it is taking multiple samples from the same closed tube or an open tube. It works by placing the tip 110 into a well in the tip wash station and dispensing the left over plasma sample plus a quantity of water (for example, 0.5 ml) from the pump 140 into the well. Water and plasma overflow from the well in known manner to waste line 192 and/or overflow tray 206. This is done after the plasma sample has been dispensed into cuvette 16. The waste lines from pumps 148 and 172 both terminate below the cover of tip wash station 40, with the ends of these lines being open to air, and with waste from these lines dripping into the waste receptacle from this tip wash. Further, an optional pinch valve 208 is shown which leads to a vent liquid trap 210. The pinch valve 208 and trap 210 allow the piercer 60 to be utilized to equalize pressure between the inside and outside of container 12 after the piercer is used to remove debris from under the stopper. However, for reasons to be discussed later, it is generally faster to have this equalization function performed by the probe 62 in a manner to be described later. Finally, an optional pressure sensor 112 is provided off of the sample vent line. This sensor allows a determination to be made as to whether the vent line is open and functioning before the probe is inserted into container 12 through stopper 14. This can be done by trying to pump air out of probe vent holes 126 while pinch valve 100 is closed. If all the vent passageways are open, sensor 212 will detect little or no pressure rise; but if the passageway are blocked, the sensor will detect an increasing air pressure. An output from the sensor can cause the system controls or processor to produce an indication that the probe vent lines need to be cleaned out and that samples aspirated while the lines are blocked may not be reliable.

Figure 14A:
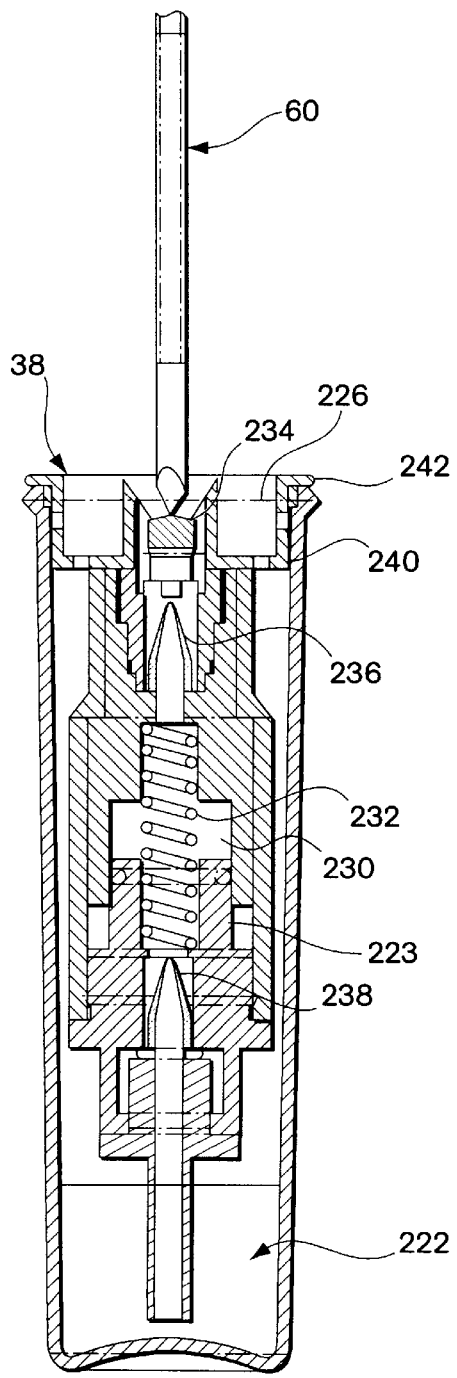
FIGS. 14A and 14B are a cutaway side view and side view respectively for alternative embodiments of a portion of a lubrication station of the type shown in FIG. 13.
Figure 14B:
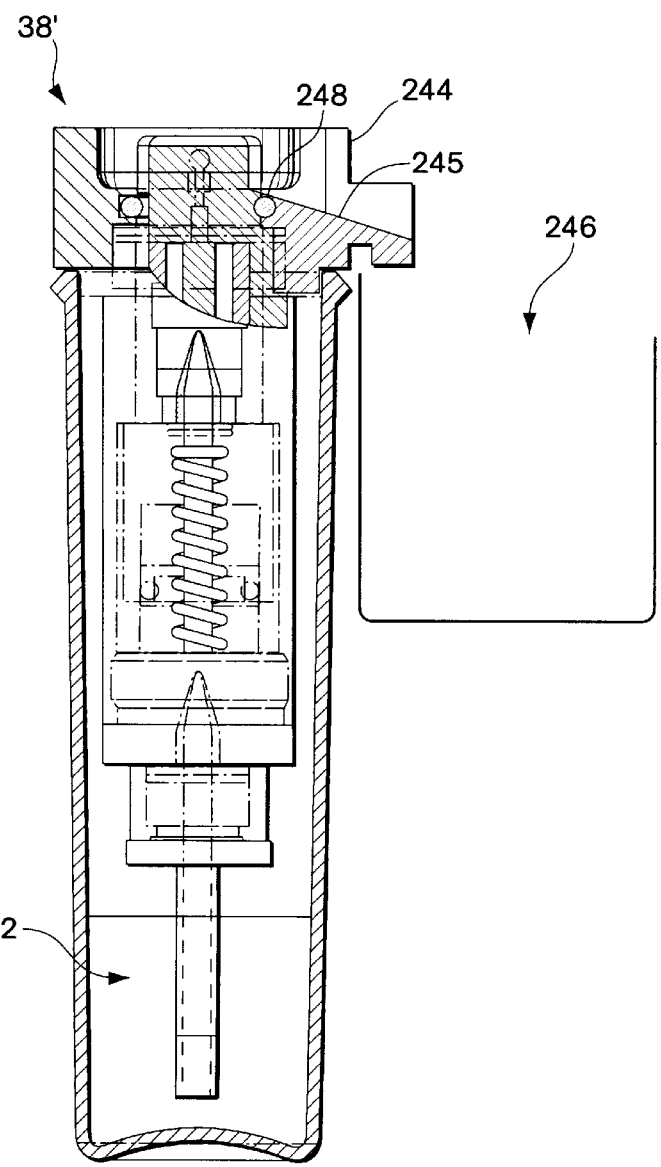

The final element of the system is lubrication station 38, which station is shown in FIGS. 13, 14A and 14B. Referring first to FIG. 13, the station 38 includes an oil reservoir or cup 220 containing silicon oil or other suitable lubricant 222. A pump mechanism 224 sits within reservoir 220 and is at least partially immersed in lubricant 222. As may be best seen in FIG. 14A, pump 220 has an upper portion 226 and a lower portion 228, with a chamber 230 therebetween. A spring 232 maintains a normal separation between upper portion 226 and lower portion 228, and thus a selected size for chamber 230. A cup 234 is provided at the top of top portion 226 against the bottom of which the tip of piercer 60 bears when the piercer is inserted into the lubrication station. A first normally-closed valve 236 separates chamber 230 from cup 234 and a second normally-closed valve 238 separates chamber 230 from the fluid 222 of the reservoir. Valve 236 is opened to permit fluid flow from chamber 230 to cup 234 when upper part 226 is moved down relative to lower part 228 under pressure from piercer 60 against the action of spring 232, and valve 238 is opened to permit fluid from reservoir 222 to flow into chamber 230 when pressure is relieved by piercer 60, permitting upper part 226 to return to its normal position under the action of spring 232 to restore chamber 230 to its normal size. For the embodiment shown in FIG. 13 and 14A, a plurality of drain holes 240 are provided around the periphery of the cap 242 mounting pump 224 in reservoir 220 to permit excess lubricant overflowing from cup 234 to drain back into the reservoir. For the embodiment shown in FIG. 14B, lubricant overflowing from cup 234 flows down an angled channel 245 which leads into a waste drain 246. A O-ring seal 248 seals the gap between top part 226 of pump 224 and the upper structure 244 which contains channel 245.

The lubrication station also has a brush holder 250 in which brushes 252 are mounted, for example four equally spaced brushes at two different levels. The brushes wipe excess oil from piercer 60 as it is being removed from the lubrication station. This excess oil is flowed back into reservoir 220 through the holes 240 (or is disposed of for the FIG. 14B embodiment in the manner shown therein).

Operation

The operation of the system 10 is as follows:

1. Positioning mechanism 30 is initially moved to its home position with probe 62 positioned over wash cup 40 and with assembly 58 in its fully raised position so that Z flag 96 is in position to be sensed by sensor 98 (FIG. 3). With the system in this position, one or more racks 18, each of which contains a plurality of sealed containers 12, may be mounted at container mounting station 22 between supports 20.

2. Mechanism 30 is then operated by the controls to position piercer 60 over lubrication station 38.

3. Assembly 58 then moves down under control of the system control by the action of gear 54 on rack 56, piercer 60 and the foot mechanism moving down under the action of gravity in the manner previously discussed with mechanism 58. When foot 68 reaches the top of brush assembly 250 as shown in FIG. 13, hole 74 in shaft 64 of the foot assembly moves up to be detected by sensor 76, causing linear solenoid 78 to be activated to lock the foot mechanism in place. This also causes rotary solenoid 86 to be activated to move pawl 84 into grove 80 of piercer 60 causing the piercer to move with assembly 58. This results in piercer 60 passing between brushes 252 and into contact with the bottom of cup 234. Continued downward movement of piercer 60 results in the upper portion 226 of pump 224 moving downward relative to the lower portion of the pump 228. This result in a decrease in the size of chamber 230 and causes valve 236 to open to permit lubricant from chamber 230 to flow into cup 234. As previously indicated, this quantity of lubricant is sufficient to cause cup 234 to fill to overflowing so that the piercer tip is fully coated with lubricant.

4. Assembly 58 is then moved upward to pull the piercer tip 164 through brushes 252, wiping off any excess lubricant, and to withdraw the piercer into foot or guard 68. Once the piercer is fully within foot 68, rotary solenoid 86 is deenergized, moving pawl 84 in a clockwise direction to remove the pawl from groove 80, and solenoid 78 is released so that detent 72 operating in conjunction with the top of assembly 58 may move the foot mechanism, including the piercer nested therein, upward to the fully raised Z position, with flag 96 detected by flag detector 98.

5. The XY positioning mechanisms of mechanism 30 then operate to position the tip of piercer 60 directly over the center of the stopper 14 for the container 12 to be accessed.

6. Assembly 58 is then moved down in a manner previously described until foot 68 makes contact with the top of the stopper 14 for the container 12 to be accessed. When this occurs, solenoid 78 and rotary solenoid 86 are again activated in a manner previously described to lock the foot mechanism against the top of the stopper and to attach the piercer 60 to move downward with assembly 58. At this time, pump 172 (FIGS. 8 and 12) is preferably activated to cause suction to be applied through tube 170 and channel 166 to vent holes 164 in the piercer tip. As the piercer moves down through the stopper, making a cut therein, the silicon oil or other lubricant from the lubrication station 38 coats the cut, inhibiting the formation of stopper debris and facilitating the passage of the piercer through the stopper. To the extent any stopper debris may be produced as the piercer passes through the stopper, such debris may also be sucked in and removed through vent holes 164. When the piercer reaches the bottom of its movement, the piercer is above the level of the fluid/plasma 113 in container 12 and holes 164 are positioned under the stopper as shown in FIG. 8 to suction out any blood cells or other blood debris which may have accumulated under the stopper and which may result in false indications of the liquid level being reached by probe 62 or in contamination of a plasma sample to be taken. The piercer remains in container 12 for a sufficient period of time to permit all potential debris to be removed, for example one second. While for one embodiment of the invention, once all debris has been fully removed, including passing through pump 172 to a waste line, pump 172 may be turned off and pinch valve 208 may be opened to permit pressure in container 12 to be equalized with that outside the container, this significantly increases the time that the piercer must be maintained in the container and therefore slows system operation. It is therefore considered preferable to do this equalization operation with the probe 62 in the manner to be described later.

7. Assembly 58 may then be raised to pull piercer 60 from container 12. During this operation, foot 68 is still locked down on cap 14 to hold the cap and container down as the piercer is being pulled up and to thus strip the piercer from the cap. It is noted that suction is still being applied by pump 172 at this time so that the stripping operation can begin while debris is still in the line and before such debris has cleared the pump; however, the pump must continue to operate until debris has fully cleared the pump and out the exit end extending from the cover of the tip wash station 40. Since the pump is continuing to operate as the piercer is being stripped, stopper debris may also be removed during the stripping operation. Once the piercer has been fully stripped from cap 14, a cut remains in the cap which may be used by the probe in a manner to be described shortly. As before, when hole 74 is detected by detector 76, the piercer mechanism is released under the action of rotary solenoid 86 and the foot mechanism is release by solenoid 78 so that the entire piercer/probe/foot mechanism assembly may be returned to its fully raised Z position.

8. The XY positioning mechanism then moves the assembly 58 to position probe 62 over the stopper and centered on the cut in the stopper made by the piercer.

9. Assembly 58 is then moved down until the foot mechanism 68 again makes contact with stopper 14 causing an output from detector 76 which operates solenoid 78 to lock the foot in place. However, in this case, piercer 68 is not locked to assembly 58 and therefore remains in foot 68 above cap 14. However, probe 62, which is attached to assembly 58 continues to move down and passes through the cut or hole formed by the piercer and into the container 12. Since the probe needs to pass only through an existing hole or cut, the probe does not need to have a sharp tip. The thin film of silicone oil left in the hole by the piercer helps to lubricate probe 62 sliding through the stopper and also prevents the formation of stopper debris by such sliding action.

At this point it should be noted that the bottom surface of foot or guard 68, which surface is in contact with the top of stopper 14, is of a size and shape such that for both piercer insertion and probe insertion, the foot is over only a single container and does not make contact with adjacent containers in the same or an adjacent rack. This is important since all of the containers may not be at the same height in a rack and a foot making contact with an adjacent container which is at a higher level could prevent proper insertion of the piercer and probe into the container, resulting in improper system operation. Further, as can be seen in the figures, when the piercer is to be inserted in a stopper, the probe is higher in foot guard 68 than the piercer so that the probe does not make contact with the stopper when the piercer is in its fully inserted position. Similarly, the piercer is not engaged by the vertical drive mechanism when the probe is to be inserted through a stopper and remains nested in the locked-down foot above the level of the stopper during probe insertion. As a result, the probe and piercer can be close together, permitting denser packing of containers at station 22.

10. The sample probe continues to move down until its tip, including vent holes 126, are below the bottom of cap 14. If at this point there is a liquid level detection from a liquid level detector to be mentioned later which is part of the probe, this indicates that all of the debris under the cap was not removed and poses a potential for sample contamination. Therefore, for a preferred embodiment, such detection will result in the sampling operation being aborted and the probe being removed from the container. At this point, the controls 11 may either reinsert the piercer 60 in an effort to remove this debris and then try inserting the probe again, or sampling/testing may merely not be performed on the container. When the probe is below cap 14, pinch valve 100 can be opened to permit air to flow through tube 152, trap 150, valve 100, joint 146, port 144, channel 124 and vent holes 126 into container 12 to equalize the pressure inside and outside the container. As indicated earlier, it is preferable to do the equalization function at this time with the probe since it does not add to the time required for the process, rather than doing the equalization function with the piercer where it does add time to the performance of the operation.

11. The probe continues to move down to the position shown in FIG. 7 with its tip under the surface of the plasma 113, but with vent holes 126 above this surface. Standard electronic liquid level sensing utilizing capacitor sensing, which sensing may be of the type disclosed in U.S. Pat. No. 5,212,992 issued May 25, 1993, can be used to detect the sample surface. A sample is then sucked up into central tube 114 by pump 140 causing the plasma level to drop. As this occurs, replacement air is drawn into container 12 above the liquid surface through pinch valve 100 and the vent holes 126. Further, as the sample is withdrawn, the probe slowly moves down to follow the lowering sample surface. For a preferred embodiment, this is accomplished by the control processor 11 knowing the quantity of fluid which is being aspirated or withdrawn, determining from this and the size of the container the drop in fluid level and then controlling the Z movement mechanism to move the probe down accordingly. Alternatively, the liquid level detection mechanism may be utilized to control this downward movement of the probe. The result is that the depth of the probe in plasma 113 is maintained between the tip of the probe and vent holes 126.

12. Assembly 58 is then raised to lift the probe from container 12, foot 68 locking down on stopper 14 to facilitate stripping of the probe from stopper 14, and the foot mechanism being released to move up with assembly 58 in response to the detection of hole 74 by detector 76.

13. Once the assembly 58 reaches its fully raised position, positioning mechanism 30 is operated so as to position the probe 62 over the cuvette 16 into which a sample is to be dispensed.

14. The Z positioning mechanism is then operated to move assembly 58 and the sample probe attached thereto down until the probe is partway into cuvette 16. Pump 140 then dispenses a precise amount of the sample from the probe tip into the cuvette in a manner known in the art. Assembly 58 and the probe are then raised to return the assembly to its fully raised or home Z position.

15. As it is known in the art, the sample originally aspirated may be utilized for a single dispensing into a cuvette or may be utilized for multiple dispensing into several cuvettes. Steps 13 and 14 may therefore be repeated multiple time until all cuvettes which are to receive samples from the aspiration done during step 11 have been completed.

16. When all samples to be dispensed from the probe have been dispensed, positioning mechanism 30 moves the probe in the XY direction so that probe 62 is directly over the dump sump area 189 of wash station 36 (FIG. 12). The sample probe is then moved down in the manner previously discussed into sump 189 and the displacement pump 140 is operated to dispense the remaining sample plus at least some of the wash fluid in tubing 114 behind the sample. This dispensing of wash fluid assures that all of the sample has in fact been dumped so as to prevent contamination of subsequent samples and the wash fluid flowing through tube 114 and opening 112 in the tip of the probe washes remaining remnants of the sample from the inside of the probe to further protect against contamination. Once the dump operation has been completed, assembly 58 and the sample probe attached thereto are returned to the fully raised Y position.

17. While if there is to be multiple dispensing from a given container 12, this would normally be done in a manner indicated for step 15 above, it is also possible to have only a single dispensing for each aspiration. In this case, if multiple samples are required from a given container, after step 16 is completed, positioning mechanism 30 would return to its home position with probe 62 over tip wash station 40. The probe tip would then be lower in the manner previously discussed into the wash station to clean the tip in standard manner. The probe and assembly 58 to which it is attached would then be raised to their fully raised Z position. Steps 8–16 would then be repeated, with the sample probe entering the container 12 through the cut made by the piercer. Depending on the material of the stopper and other factors, this step may be repeated a number of times, as required, before the stopper condition would be such that further passage of the probe through the cut would risk sufficient stopper debris being generated as to make sample aspiration unreliable.

18. After step 16 is performed for the last time for a given container 12, the XY positioning mechanism 30 is operated so that sample probe 62 is directly over its wash well 182 and piercer 60 is directly over its wash well 180. Assembly 58 is then moved down until pawl 84 is adjacent groove 82 in the piercer 60, this being determined by the control microprocessor counting steps from the stepper motor 55 after sensor 76 sees hole 74. At a predetermined number of steps, solenoid 86 is energized to engage pawl 84 in this groove. Assembly 58 then continues to move down until both the piercer and probe are fully extended into their respective wash wells as shown in FIG. 11 with the probe being below the piercer.

19. As probe 62 moves down into its well 182, pump 194 starts to pump wash fluid, normally water, in at the top of the well and, with pinch valve 100 closed, pump 148 starts pumping air into the well through holes 126. When probe 62 completes its downward motion into its well, positive displacement pump 140 dispenses additional wash fluid through line 114 and probe tip 112. These combined wash inputs fill well 182 and wash the exterior of the probe, the wash fluid flowing therethrough also washing the interior of the probe. When pump 194 stops, pump 200 is actuated to pump the wash fluid out of the well and onto the waste line 192. During the entire time that wash fluid is in well 182, air is slowly pumped out through vents 126 to prevent wash fluid from getting into the vents and thus into air channel 124. At the same time that the sample probe is getting washed, piercer 60 is getting washed in its well 180. This is accomplished by spraying multiple jets of wash fluid on its exterior at least as it moves out of the well. This wash fluid is pumped into the well by pumps 186A and 186B. At all times that piercer 60 is in its well 180, pump 172 slowly pumps air out through vent holes 164 so that wash fluid is prevented from getting into the vents and into channels 166 and 170. Water may be pumped during the entire wash cycle; however, for a preferred embodiment, washing, at least for probe 62, occurs for roughly half the wash cycle, and air is pumped over the probe for the remainder of the cycle to dry the probe. Air drying could also be done for the piercer.

20. When the wash cycle is completed, assembly 58 is raised in a manner previously discussed to move both piercer 60 and probe 62 out of the wash station and to return them to their home positions in foot 68. Assembly 58 is then returned to its fully raised position and the positioning mechanism is returned to its home position.

21. At this point the operation may return to step 2 so that aspiration and dispensing operations may begin for another container. Steps 2–20 will then be repeated for that container as appropriate and the sequence of operations will be repeated until accessing and aspiration of all containers to be sampled has been completed. It should be noted that at any point in the operation, an additional aspiration or sampling can be performed on a container which was previously sampled. In this case, steps 2–7 would not be repeated and the operation for this container would start with step 8, with the probe mechanism over the cut previously made. Such accesses by the probe through a cut can be performed a number of times until the condition of the stopper would make such passing of the probe through the stopper no longer desirable. When sampling is completed on all containers at container mounting station 22, step 1 may be repeated, with the racks containing the used containers being removed and racks with new containers to be sampled being mounted at the station.

A system for rapidly and accurately sampling sealed containers while minimizing potential contamination problems is thus provided. For a preferred embodiment, steps 2–20 can be completed in approximately 14–15 seconds, permitting approximately four sampling operations per minute.

While the invention has been described above with respect to a preferred embodiment utilized for performing plasma analysis, it is apparent that the invention could find other applications for sampling additional bodily fluid such as serum. More generally, the teachings of this invention might find application in any situation where access is required to the contents of a container which is piercably sealed. Further, while specific mechanisms are shown for performing the various positioning, lubricating, washing, probing, piercing and other functions, these mechanisms are by way of example only and other mechanisms adapted for performing these various functions may be utilized. Further, while the lubricating station shown in FIGS. 13, 14A and 14B is shown utilized for lubricating the piercer of this invention, this device may be utilized to coat a lubricant or other required liquid on a pointed stylus in other applications. Thus, while the invention has been particularly shown and described above with reference to a preferred embodiment, the foregoing other changes in form and detail may be made therein by one skilled in the art while still remaining within the spirit and scope of the invention and the invention is only to be limited by the following claims.

We claim:

1. Apparatus for accessing fluid in a container which container is sealed by a piercable seal comprising:

a piercer;

a probe having a hollow tube into which said fluid is to be drawn;

a first mechanism for moving both the piercer and the probe in the Z direction perpendicular to said seal, at least one of said piercer and probe not normally being attached to move with the first mechanism, but being selectively attachable to move therewith;

a second mechanism which moves the first mechanism, including the piercer and the probe in X and Y directions substantially perpendicular to the Z direction; and controls for operating said first and second mechanisms to have said piercer pierce the seal of a container while the probe is maintained a selected distance above the seal to withdraw the piercer from the seal, leaving a cut, and to then have the probe pass through said cut in the seal to enter said fluid while the piercer is maintained at a selected distance above the seal.

2. Apparatus as claimed in claim 1 including a foot through which said piercer and probe pass, said foot being at the bottom of a foot mechanism which is mounted to normally move with said first mechanism in the Z direction, said controls locking said foot mechanism against Z direction movement when the foot is lowered into contact with the seal of a container and releasing the foot mechanism to again move with the first mechanism when the first mechanism has risen to a predetermined position.

3. Apparatus as claimed in claim 2 wherein there are a plurality of said containers to be accessed which containers are mounted adjacent each other with a selected space therebetween, and wherein the foot has a lower seal-contacting surface of a size and shape such that said lower surface contacts only the seal for the container being accessed and does not contact the seal for an adjacent container when the foot is lowered for the piercing of the seal by the piercer and when the foot is lowered for entry of the probe through the seal.

4. Apparatus as claimed in claim 2 wherein said foot mechanism and at least one of said piercer and said probe are normally moved downward in the Z direction by gravity, such downward movement being restrained by detents limiting how far below the first mechanism they may fall, a first locking component operated by said controls for locking said foot mechanism against Z direction movement under selected conditions, and a second locking component operated by said controls under selected conditions for locking the at least one of said piercer and said probe to the first mechanism to move therewith in the Z direction.

5. Apparatus as claimed in claim 4 wherein said piercer normally rests within, and is detented against independent downward movement by, said foot, and wherein when said second locking component locks the piercer to the first mechanism, the first mechanism moves the piercer downward and upward through the foot.

6. Apparatus as claimed in claim 1 including a lubrication station, said controls operating said first and second mechanisms to position the piercer over and to dip the piercer into the lubrication station before moving the piercer to pierce said seal.

7. Apparatus as claimed in claim 6 wherein said lubrication station includes means for controlling the depth to which said piercer is lubricated.

8. Apparatus as claimed in claim 7 wherein said lubricating station includes means for removing excess lubricant from the piercer before the piercer is moved to pierce the seal.

9. Apparatus as claimed in claim 1 wherein said piercer has a plurality of vent holes circumferentially positioned above its tip and a channel leading from the vent holes out of the piercer; and including a suction source connected to said channel, said controls operating said suction source to apply suction to the vent holes from a time before the piercer pierces the seal to a time after the piercer is removed from the seal.

10. Apparatus as claimed in claim 9 wherein said piercer, including said vent holes, have smooth rounded edges to minimize abrasion of the seal as the piercer is passed therethrough.

11. Apparatus as claimed in claim 1 wherein said probe is part of a liquid level detection mechanism, and wherein said controls are operative in response to an output from said liquid level detection mechanism before the probe has advanced sufficiently into the container to contact fluid for aborting accessing fluid from the container by the probe.

12. Apparatus as claimed in claim 1 wherein said probe is part of a liquid level detection mechanism, wherein said probe has vent holes a selected distance above its tip through which pressure inside and outside the container are equalized when the probe enters the container, and wherein said controls operate with said liquid level detection mechanism to control said first mechanism so that the probe enters fluid in the container to a depth between the vent holes and the probe tip and to lower the probe as fluid is removed by the probe to maintain the depth of the probe in the fluid within such range.

13. Apparatus as claimed in claim 1 including a wash station for said piercer and probe, said controls operating the first mechanism and the second mechanism to move the piercer and probe over and to immerse the piercer and probe in the wash station when accessing operations for a container have been completed.

14. Apparatus as claimed in claim 13 wherein each of said piercer and probe has vent holes leading to a channel therein, and including an air pressure source connected to each said channel, said controls operating each said air pressure source to blow air out through said vent holes when the piercer and probe are immersed in the wash station, thereby keeping wash fluid out of the holes and channels.

15. Apparatus as claimed in claim 13 wherein said wash station has a separate well for the piercer and the probe, and wherein said controls cause a washing fluid to flow through each well during a first part of a wash cycle to wash the element therein, and cause air to be flowed through the well for at least the probe for a second part of the wash cycle to dry the corresponding element.

16. Apparatus for accessing fluid in a container sealed by a piercable seal comprising:

a piercer;

a probe having a hollow tube into which said fluid is to be drawn;

a first mechanism for moving both the piercer and the probe in the Z direction perpendicular to said seal;

a second mechanism which moves the first mechanism, including the piercer and probe in X and Y directions substantially perpendicular to the Z direction;

a foot through which said piercer and probe independently pass, said foot being at the bottom of a foot mechanism which is mounted to normally move with said first mechanism in the Z direction and with said second mechanism in the X and Y directions; and controls for operating said first and second mechanisms to lower said foot into contact with the seal, only said piercer passing through the foot to pierce the seal of a container, to withdraw the piercer from the seal, leaving a cut in the seal, and to have said foot again brought into contact with said seal, only the probe passing through said cut in the seal to enter said fluid, said controls locking said foot mechanism against Z direction movement each time the foot is lowered into contact with the seal of a container and releasing the foot mechanism to again move with the first mechanism each time the first mechanism has risen to a predetermined position.

17. Apparatus as claimed in claim 16 wherein there are a plurality of said containers to be accessed, which containers are mounted adjacent each other with a selected space therebetween, and wherein the foot has a lower seal-contacting surface of a size and shape such that said lower surface contacts only the seal for the container being accessed and does not contact the seal for an adjacent container when the foot is lowered for the piercing of the seal by the piercer and when the foot is lowered for entry of the probe through the seal.

18. Apparatus as claimed in claim 16 wherein said foot mechanism and at least one of said piercer and said probe are normally moved downward in the Z direction by gravity, such downward movement being restrained by detents limiting how far below the first mechanism they may fall, a first locking component operated by said controls for locking said foot mechanism against Z direction movement under selected conditions, and a second locking component operated by said controls under selected condition for locking the at least one of said piercer and said probe to the first mechanism to move therewith in the Z direction.

19. Apparatus as claimed in claim 18 wherein said piercer normally rests within, and is detented against independent downward movement by, said foot, and wherein when said second locking component locks the piercer to the first mechanism, the first mechanism moving the piercer downward and upward through the foot.

20. Apparatus for accessing fluid in a container sealed by a piercable seal comprising:

a piercer;

a probe having a hollow tube into which said fluid is to be drawn;

a first mechanism for moving both the piercer and the probe in the Z direction perpendicular to said seal;

a second mechanism which moves the first mechanism, including the piercer and probe in X and Y directions substantially perpendicular to the Z direction;

a lubrication station; and controls for operating said first and second mechanisms to have said piercer pierce the seal of a container, to withdraw the piercer from the seal, leaving a cut in the seal, and to then have the probe pass through said cut in the seal to enter said fluid, the controls operating said first and second mechanism to position the piercer over and to dip the piercer into the lubrication station before moving the piercer to pierce said seal.

21. Apparatus as claimed in claim 20 wherein said lubrication station includes means for controlling the depth to which said piercer is lubricated.

22. Apparatus as claimed in claim 20 wherein said lubrication station includes means for removing excess lubricant from the piercer before the piercer is moved to pierce the seal.

23. Apparatus for accessing fluid in a container sealed by a piercable seal comprising:

a piercer having a plurality of vent holes circumferentially positioned above its tip and a channel leading from the vent holes out of the piercer;

a suction source connected to said channel;

a probe having a hollow tube into which said fluid is to be drawn;

a first mechanism for moving both the piercer and the probe in the Z direction perpendicular to said seal;

a second mechanism which moves the first mechanism, including the piercer and probe in X and Y directions substantially perpendicular to the Z direction; and controls for operating said first and second mechanisms to have said piercer pierce the seal of a container, to withdraw the piercer from the seal, leaving a cut in the seal, and to then have the probe pass through said cut in the seal to enter said fluid, the controls operating said suction source to apply suction to the vent holes from a time before the piercer pierces the seal to a time after the piercer is removed from the seal.

24. Apparatus as claimed in claim 23 wherein said piercer, including said vent holes, have smooth rounded edges to minimize abrasion of the seal as the piercer is passed therethrough.

25. Apparatus for accessing fluid in a container which container is sealed by a piercable seal comprising:

a tipped component for piercing said seal;

a first mechanism for moving the component in a Z direction substantially perpendicular to said seal, said component not normally being attached to move with the first mechanism, but being selectively attachable to move therewith;

a foot through which said component passes, said foot being at the bottom of a foot mechanism which is mounted to normally move with said first mechanism in the Z direction;

a second mechanism which moves the first mechanism, including the component and the foot, in at least one direction substantially perpendicular to the Z direction; and controls for operating said second mechanism to position said component over the seal of a container, for operating the first mechanism to then lower the component to pass through the seal, and for subsequently operating the first mechanism to raise the component through the seal to remove it from the container, said controls locking said foot mechanism to prevent further Z direction movement with the first mechanism when the foot is lowered into contact with the seal of a container, and releasing the foot mechanism to again move with the first mechanism when the first mechanism has risen to a predetermined position sufficient to fully remove the component from the container, including the seal, the locked foot mechanism facilitating striping of the component from the seal.

26. Apparatus as claimed in claim 25 wherein there are a plurality of said containers to be accessed which containers are mounted adjacent each other with a selected space therebetween, and wherein the foot has a seal-contacting surface of a size and shape such that said surface contacts only the seal for the container being accessed and does not contact the seal for an adjacent container when the foot is lowered for entry of the component through the seal.

27. Apparatus as claimed in claim 26 wherein said foot mechanism and said component are normally moved downward in the Z direction by gravity, such downward movement being restrained by detents limiting how far below the first mechanism they may fall, a first locking component operated by said controls for locking said foot mechanism against Z direction movement under selected conditions, and a second locking component operated by said controls under selected conditions for locking the component to the first mechanism to move therewith in the Z direction.

* * * * *